United States Patent
Adamy et al.

(10) Patent No.: US 6,471,948 B1
(45) Date of Patent: Oct. 29, 2002

(54) TOOTHPASTE COMPOSITIONS CONTAINING CETYLPYRIDINIUM CHLORIDE

(75) Inventors: Steven T. Adamy, Hamilton, NJ (US); Francis R. Cala, Highland, NJ (US)

(73) Assignee: Church & Dwight Co. Inc., Princeton, NJ (US)

( * ) Notice: Subject to any disclaimer, the term of this patent is extended or adjusted under 35 U.S.C. 154(b) by 0 days.

(21) Appl. No.: 09/533,293

(22) Filed: Mar. 22, 2000

(51) Int. Cl.7 .............................. A61K 7/16; A61K 7/22
(52) U.S. Cl. ............................................ 424/54; 424/49
(58) Field of Search ...................... 424/49–58

(56) References Cited

U.S. PATENT DOCUMENTS

| | | | | | |
|---|---|---|---|---|---|
| 4,389,394 A | * | 6/1983 | Drucker | ............ | 424/49 |
| 4,405,654 A | * | 9/1983 | Lee | ............ | 424/49 |
| 4,839,158 A | * | 6/1989 | Michaels | ............ | 424/54 |
| 4,971,797 A | * | 11/1990 | Cherukuri et al. | ......... | 424/440 |
| 5,158,763 A | * | 10/1992 | Gaffar et al. | .......... | 424/54 |
| 5,370,881 A | * | 12/1994 | Fuisz | ................ | 426/5 |
| 5,374,368 A |   | 12/1994 | Hauschild | | |
| 5,376,360 A |   | 12/1994 | Domke et al. | | |
| 5,622,689 A | * | 4/1997 | Lukacovic | ............ | 424/52 |
| 5,849,268 A | * | 12/1998 | Lukacovic | ............ | 424/52 |
| 5,849,271 A | * | 12/1998 | Lukacovic | ............ | 424/49 |
| 5,948,390 A | * | 9/1999 | Nelson et al. | ........... | 424/54 |

FOREIGN PATENT DOCUMENTS

| | | | |
|---|---|---|---|
| EP | 9408 A1 | * | 4/1980 |
| EP | 422 803 A2 | * | 4/1991 |
| EP | 480 811 A2 | * | 4/1992 |
| EP | 507 598 | * | 10/1992 |
| EP | 920 857 A2 | * | 6/1999 |
| WO | 90/15592 | * | 12/1990 |
| WO | 97/462 17 | * | 12/1997 |

* cited by examiner

Primary Examiner—Shep K. Rose
(74) Attorney, Agent, or Firm—Watov & Kipnes, P.C.

(57) ABSTRACT

A toothpaste composition containing an effective amount of cetylpyridinium chloride and a mixture of toothpaste forming ingredients including at least one amphoteric surfactant and optionally at least one sweetener.

12 Claims, No Drawings

TOOTHPASTE COMPOSITIONS CONTAINING CETYLPYRIDINIUM CHLORIDE

FIELD OF THE INVENTION

The present invention is directed to toothpaste compositions containing cetylpyridinium chloride as an active antibacterial agent which may be used to inhibit the formation of plaque. The composition contains the active agent and at least one surfactant in which the components of the composition do not substantially interfere with the cetylpyridinium chloride and thereby enable the active agent to effectively bind to the teeth to perform its antibacterial function.

BACKGROUND OF THE INVENTION

Cetylpyridinium chloride is well known as an antibacterial agent especially for the inhibition of plaque formation. This antibacterial agent has been used in commercial liquid mouthwash products such as Scope® and Cepacol®. The environment of the commercial mouthwash products enables cetylpyridinium chloride to freely contact those oral surfaces which may harbor unwanted microorganisms. However, cetylpyridinium chloride is not effectively employed in many systems because of its tendency to complex with components which carry a negative charge. When bound in this manner, the cetylpyridinium chloride is unavailable for effective contact with tooth surfaces and thereby renders the active agent ineffective for its intended purpose.

Toothpaste compositions typically include an anionic surfactant and often include an artificial sweetener. These components are capable of binding with cetylpyridinium chloride to thereby render the antibacterial agent ineffective. Other components typically found in a toothpaste composition such as an abrasive material are also typically capable of binding to cetylpyridinium chloride.

It would be an advance in the art if toothpaste compositions contained components which did not render cetylpyridinium chloride ineffective but still provide the toothpaste composition with those characteristics which make the toothpaste composition effective as part of oral hygiene care.

SUMMARY OF THE INVENTION

The present invention is generally directed to a toothpaste composition in which cetylpyridinium chloride is present as an antibacterial agent as part of an effective oral hygiene program. In a particular aspect of the present invention, there is provided a toothpaste composition comprising:
  a) an antibacterial effective amount of cetylpyridinium chloride; and
  b) a mixture of toothpaste forming components, including at least one surfactant and optionally at least one sweetener, the sweetener and/or surfactant alone or in combination permitting the cetylpyridinium chloride to effectively bind to the teeth to perform an antibacterial function.

DETAILED DESCRIPTION OF THE INVENTION

The toothpaste composition of the present invention includes an antibacterial effective amount of cetylpyridinium chloride and other toothpaste components which do not materially prevent the cetylpyridinium chloride from binding to tooth surfaces to perform an antibacterial function. The phrase "do not materially prevent" as used herein means that a sufficient amount of cetylpyridinium chloride is available to bind to tooth surfaces to perform an antibacterial function.

Toothpaste compositions contain a number of components which are either active in performing a particular function related to the oral care system afforded by the toothpaste or to a passive function which is employed to provide a composition to enable the active components to perform their function. Examples of active components are tooth whiteners, antibacterial agents, abrasives or polishing materials and the like. Examples of passive components include organic surfactants which assist thorough and complete dispersion of one or more active agents, sweeteners, is preservatives and the like. The organic surfactants may and usually do provide both active cleaning activities as well as passive functions.

The toothpaste compositions of the present invention may vary widely as to the components, but the toothpaste forming components which typically include at least one surfactant and optionally at least one sweetener do not materially prevent cetylpyridinium chloride from binding to tooth surfaces.

Cetylpyridinium chloride is cationic in nature and therefore is attracted to negative surfaces. Tooth surfaces typically have a negative charge and therefore there is a natural attraction of cetylpyridinium chloride for tooth surfaces. However, many conventional toothpaste forming components are anionic and therefore possess a negative charge causing such components to bind to cetylpyridinium chloride and therefore make it unavailable for binding to tooth surfaces.

In accordance with one aspect of the present invention, it has been discovered that the employment of certain amphoteric surfactants eliminates a major portion of the interference of the other components with cetylpyridinium chloride activity. By employing such surfactants, the surfactant performs its natural function without interfering with the cetylpyridinium chloride (the cetylpyridinium chloride and its antibacterial properties are thereby not effectively removed from the toothpaste composition).

In a second aspect of the invention, certain sweeteners have been found to actually disrupt cetylpyridinium chloride activity in the presence of surfactants as compared to the same situation in the absence of such particular sweeteners.

One class of preferred surfactants for use in the present invention are those encompassed by Formula I

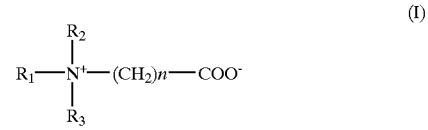

(I)

where $R_1$ and $R_2$ are independently an alkyl group of 1–4 carbon atoms, preferably they are the same, and most preferably they are each methyl;

n is an integer of from 1–4;

$R_3$ is a group $R_a$ or $(R_a—C(O)NH_2)—(CH_2)_m$ in which m is an integer of from 1–4, and $R_a$ is an alkyl of 8–20 carbons. $R_a$ is most preferably coco (i.e., a mixture $C_{14}$ to $C_{16}$) and m is preferably 3.

The preferred surfactants of those encompassed by Formula I include coco betaine and cocamidopropyl betaine and combinations thereof.

Another class of surfactants which are particularly suitable for use in the present invention are amine oxides encompassed by Formula II

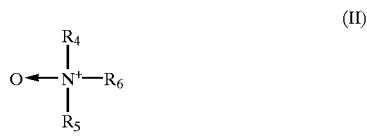

(II)

wherein $R_4$ and $R_5$ which may be the same or different are each independently selected from an alkyl group having 1 to 4 carbon atoms, and $R_6$ is an alkyl group having from 8 to 12 carbon atoms, which is unsubstituted or substituted by at least one $C_1–C_4$ alkyl group.

Some specific examples of amine oxides for use in the present invention include dodecyl-methylamine oxide, cocamidopropyl dimethylamine oxide, ether amine oxides and the like. The preferred compounds are N,N-dimethyldodecylamine oxide, N,N-dimethyidecylamine oxide, and N,N-dimethyloctylamine oxide, respectively.

The present toothpaste composition may optionally contain a sweetener which does not materially prevent the cetylpyridinium chloride from binding to tooth surfaces. Desirable sweeteners are those which are not negatively charged and includes those which are cationic, non-ionic or amphoteric in nature. A preferred sweetener is Sucralose manufactured by McNeil Labs of New Brunswick, N.J.

Other components which may be incorporated into the toothpaste composition of the present invention include whiteners, flavorants, humectants, desensitizing agents, thickening agents, abrasives, fluoride providing compounds and the like. Suitable non-ionic thickening agents include $(C_{2-6})$ alkylene oxide modified $(C_{1-6})$ alkylcellulose ethers such as hydroxy-ethylcellulose, hydroxy-propylcellulose, hydroxy-propylmethylcellulose and mixtures thereof. Suitable cationic thickening agents include quaternary cellulose derivatives, guar gum derivatives and the like.

Abrasive materials include certain phosphates such as sodium metaphosphate, potassium metaphosphate, tricalcium phosphate, dicalcium phosphate dihydrate, anyhydrous dicalcium phosphate, calcium pyrophosphate, zinc orthophosphate, alumina, hydrated alumina, aluminum silicate, bentonite, calcium carbonate, sodium bicarbonate and the like.

Fluoride-providing compounds include inorganic fluoride salts, such as soluble alkali metal, alkaline earthmetal and heavy metal salts, for example, sodium fluoride, potassium fluoride, ammonium fluoride, lead fluoride, copper fluoride, zinc fluoride, tin fluoride, barium fluoride, sodium fluorosilicate, ammonium fluorosilicate, sodium fluorozirconate, sodium monofluorophosphate, aluminum mono-endifluorophosphate and the like.

Humectants include glycerin, sorbitol, polyethylene glycol, and the like.

Desensitizing agents include potassium salts, and strontium salts especially potassium nitrate, strontium chloride and the like.

In accordance with a preferred aspect of the present invention a cetylpyridinium chloride-containing toothpaste composition containing decylamine oxide alone or in combination with a sweetener, especially sucralose provides significant availability of the antibacterial agent to bind to tooth surfaces. The surfactant cocamidopropyl betaine in combination with Sucralese provides another highly effective toothpaste composition.

EXAMPLE 1

Absorption of Cetylpyridinum Chloride in the Presence of Surfactants

Disks of hydroxyapatite (HAP) measuring 0.5 inch diameter and 0.04 inch thick were obtained from Clarkson Chromatography Products (Williamsport, Penn.). The disks were hydrated in deionized water for one hour and then allowed to air dry.

A 1% dispersion of bovine submaxillary mucin (type 1S, from Sigma) was then prepared. The HAP disks were then soaked in the 1% mucin dispersion overnight. The disks were then allowed to air dry for al least 2 hours. These disks, composed of HAP on which was deposited a layer of mucin, represented an oral surface.

Cetylpyridinium chloride adsorption was tested by soaking the disks in a test solution. The test solutions contained 0.125% cetylpyridinium chloride and 0.9% of each of the surfactants shown in Table 1. The disks were soaked in 5 ml of the test solution for 10 minutes in a polystyrene petri dish (35 mm diameter×10 mm deep, from Becton Dickinson). The disks were then removed, rinsed for 3 seconds with deionized water on each side with a wash bottle.

Adsorbed cetylpyridinium chloride was extracted by soaking the disks in a solution used as a mobile phase for cetylpyridinium chloride detection in liquid chromatography. The extractant solution is composed of 60 parts of a 20 mM phosphate buffer and 40 parts methanol, in which is dissolved 30 mM cetyltrimethylammonium bromide. The disks were soaked in 5 ml of the extractant solution for 2 hours. The extractant solution was then analyzed for cetylpyridinium chloride using high-pressure liquid chromatography.

The results are shown in Table 1.

TABLE 1

| Surfactant | Surfactant Type | CPC adsorbed (µg/disk) | % Activity |
|---|---|---|---|
| None | — | 59.4 | 100 |
| Poloxypol 1220 (nonionic EO-PO copolymer surfactant) | Nonionic | 21.0 | 35.4 |
| Sodium lauryl sarcosinate | Anionic | 5.9 | 9.9 |
| Cocoamphodiacetate | Amphoteric | 8.0 | 13.5 |
| Cocamidopropyl betaine | Amphoteric | 41.8 | 70.4 |
| Sodium lauryl sulfate | Anionic | 2.5 | 4.2 |

As shown in Table 1, cetylpyridinium chloride was 100% absorbed by the disks in the absence of surfactant because the surfactant did not impede binding to the synthetic tooth surface.

In the presence of anionic surfactants, sodium lauryl sarcosinate and sodium lauryl sulfate, there was very little cetylpyridinium chloride absorbed. In the presence of amphoteric and nonionic surfactants, the amount of cetylpyridinium chloride absorbed was at least 35% higher than the anionic surfactant treated disks. Cocamidopropyl betaine exhibited clearly superior absorption results.

EXAMPLE 2

The test performed in Example 1 was repeated using the surfactants shown in Table 2 below and each test solution also contained 0.125% by weight of sodium bicarbonate.

TABLE 2

| Surfactant | CPC adsorbed (μg/disk) | % Activity |
| --- | --- | --- |
| Dodecylamine oxide | 41.1 | 65.9 |
| Decylamine oxide | 39.1 | 62.7 |
| Octylamine oxide | 47.4 | 76.0 |
| Cocobetaine | 48.8 | 78.2 |
| Cocamidopropyl betaine | 41.2 | 66.0 |
| Dodecyl-Amphodiacetate | 10.6 | 17.0 |
| Dodecyl-Iminodipropionate | 7.4 | 11.9 |
| Alkylimidazoline derivative | 23.8 | 38.1 |
| None | 62.4 | 100 |

As shown in Table 2, the amine oxide and betaine surfactants enabled significantly larger amounts of cetylpyridinium chloride to be absorbed as compared with negatively charged surfactants.

EXAMPLE 3

Toothpaste Compositions Containing Cetylpyridinium Chloride, Surfactants and Sweeteners Hydroxyapatite disks were prepared as described in Example 1. Six samples of toothpaste compositions having the compositions shown in Table 3 were prepared in the following manner. Water and glycerin were combined and mixed. Natrasol 250M was added to the mixture and stirred for about 20 minutes. The surfactant was added and the mixture stirred for 20 minutes followed by the sequential steps of addition and mixing of the sodium monofluorophosphate, flavorant, cetylpyridinium chloride, sweetener, sodium bicarbonate, aluminum oxide and calcium carbonate followed by mixing of the final mixture until even distribution of the components, and thereafter for about 30 minutes.

Each of the compositions was tested for cetylpyridinium chloride absorption as described in Example 1. The results are shown in Table 4.

TABLE 3

| Component | 1 | 2 | 3 | 4 | 5 | 6 |
| --- | --- | --- | --- | --- | --- | --- |
| Glycerin | 15 | 15 | 15 | 15 | 15 | 15 |
| Natrosol 250M | 1 | 1 | 1 | 1 | 1 | 1 |
| Water | 25 | 25 | 25 | 25 | 25 | 25 |
| Na-MFP | 1.153 | 1.153 | 1.153 | 1.153 | 1.153 | 1.153 |
| CPC-1H2O | 0.5 | 0.5 | 0.5 | 0.5 | 0.5 | 0.5 |
| Al2O3 | 7 | 7 | 7 | 7 | 7 | 7 |
| NaHCO3 | 5 | 5 | 5 | 5 | 5 | 5 |
| CaCO3 | 41.047 | 41.047 | 41.047 | 41.047 | 41.047 | 41.047 |
| Flavor | 1 | 1 | 1 | 1 | 1 | 1 |
| TEGO - ZF (CAP-betaine) (30% Al)* | 3 | | | 3 | | |
| Mirataine H2C-HA (30% Al)** | | 3 | | | 3 | |
| Mackamine C-10 (30% Al)*** | | | 3 | | | 3 |
| Na-Saccharin | 0.3 | 0.3 | 0.3 | | | |
| Sucralose | | | | 0.3 | 0.3 | 0.3 |
| TOTAL | 100 | 100 | 100 | 100 | 100 | 100 |

*TEGO-AF is cocamidopropylbetaine
**Mirataine H2C-HA is dodecylaminedipropionate
***Mackamine C-10 is N,N-dimethyldecylamine oxide

TABLE 4

| Formula | Sweetener + Surfactant | CPC adsorbed (μg/disk) | % Activity |
| --- | --- | --- | --- |
| 1 | Sodium Saccharin + cocamidopropyl betaine | 3.4 | 7.6 |
| 2 | Sodium Saccharin + Dodecyl iminodipropionate | 2.9 | 6.5 |
| 3 | Sodium Saccharin + Decylamine oxide | 18.2 | 40.8 |
| 4 | Sucralose + cocamidopropyl betaine | 14.3 | 32.1 |
| 5 | Sucralose + Dodecyl iminodipropionate | 3.4 | 7.6 |
| 6 | Sucralose + Decylamine oxide | 17.1 | 38.3 |
| 7 | None | 44.6 | 100.0 |

As shown in Table 4, the best cetylpyridinium chloride absorption by the synyetic tooth surfaces was exhibited when both the sweetener and surfactant are chosen in accordance with the present invention thereby enabling a high level cetylpridinium chloride absorption. Formula 3 which includes a surfactant of the present invention but not the sweetener showed surprising comparable cetylpyridinium chloride adsorption.

EXAMPLE 4

Toothpaste compositions identified by Samples 8–23 having the compositions shown in Table 3 except that the sweetener and/or surfactant were changed as shown in Table 5. Each of the compositions was tested for cetylpyridinium chloride absorption as described in Example 1. The results are shown in Table 5.

TABLE 5

CAP-betaine = cocamidopropyl betaine
C12l-diP = dodecyl iminodipropionate
C10AO = decyl amine oxide
SLS = sodium lauryl sulfate

| Class | Sample | Surfactant | Sweetener | CPC adsorbed (μg/disk) | % Activity (i.e. amount CPC/max CPC adsorbed) |
|---|---|---|---|---|---|
| No surfactant or sweetener | 22 | — | — | 11.7 | 30.0 |
| Surfactant but no sweetener | 16 | CAP-betaine | — | 13.1 | 34.6 |
| | 17 | C12l-diP | — | 3.8 | 10.0 |
| | 18 | C10AO | — | 15.8 | 41.7 |
| | 19 | SLS | — | 3.8 | 10.0 |
| Sweetener but no surfactant | 20 | — | Saccharin | 8.1 | 21.4 |
| | 21 | — | Sucralose | 11.5 | 30.3 |
| Surfactant and sweetener | 8 | CAP-betaine | Saccharin | 6.4 | 16.9 |
| | 9 | C12l-diP | Saccharin | 3.8 | 10.0 |
| | 10 | C10AO | Saccharin | 18.6 | 49.1 |
| | 14 | SLS | Saccharin | 3.8 | 10.0 |
| | 11 | CAP-betaine | Sucralose | 16.2 | 42.7 |
| | 12 | C12l-diP | Sucralose | 4.3 | 11.3 |
| | 13 | C10AO | Sucralose | 19.2 | 50.7 |
| | 15 | SLS | Sucralose | 3.8 | 10.0 |
| CPC solution* in water | 23 | — | — | 37.9 | 100 |

*0.125% by weight of CPC and 0.125% by weight of sodium bicarbonate in water

Samples 20 and 21 containing sweetener only, show similar results for sucralose and saccharin. This suggests that there were additional components (like $CaCO_3$ and $Al_2O_3$) which inhibited cetylpyridinium chloride adsorption.

Samples 8–15 containing surfactant and sweetener are consistent with the behavior that when either saccharin or a negatively charged surfactant was added, the adsorption of cetylpyridinium chloride was low. However, the adsorption in systems containing decylamine oxide (C10AO) were higher, even when saccharin was present. This may have been due to the positively charged amine oxide interacting with saccharin (or other negatively charged species), thus reducing the CPC-saccharin interaction (a "competitive inhibition" effect).

EXAMPLE 5

Toothpaste compositions 24–30 including the components shown in Table 6 were prepared with one or both of the amine oxide and sweetener components as shown in Table 7. A control sample was prepared and is identified as Sample 31. Each sample was tested for cetylpyridinium chloride absorption activity as described in Example 1. The results are shown in Table 7.

TABLE 6

| Component | Amount (Wt. %) |
|---|---|
| Glycerin | 15 |
| Natrosol 250 M | 1 |
| Na-MFP | 1.153 |
| CPC monohydrate | 0.5 |
| $Al_2O_3$ | 7 |
| $NaHCO_3$ | 5 |
| $CaCO_3$ | 41.047 |
| Flavor 78561.04/T | 1 |
| Decylamine oxide | 0.9 |
| Sweetener | 0.3 |
| Water | q.s. to 100% |

TABLE 7

| Sample | Description | CPC adsorbed (μg/disk) | % Activity (amount CPC/max CPC adsorbed) | % Increase due to addition of C10A0* | Previous % Increase due to addition of C10A0 | Ave. % Increase |
|---|---|---|---|---|---|---|
| 24 | C10AO Alone | 9.1 | 20.4 | | | |
| 25 | Sacc. Alone | 5.3 | 11.8 | | | |
| 26 | Ace-K Alone | 4.5 | 10.1 | | | |
| 27 | Suc. Alone | 7.2 | 16.2 | | | |
| 28 | C10AO + Sacc. | 8.9 | 20.0 | 69.5 | 129.6 | 99.6 |

TABLE 7-continued

| Sample | Description | CPC adsorbed (μg/disk) | % Activity (amount CPC/max CPC adsorbed) | % Increase due to addition of C10AO* | Previous % Increase due to addition of C10AO | Ave. % Increase |
|---|---|---|---|---|---|---|
| 29 | C10AO + Ace-K | 9.2 | 20.7 | 104.2 | | 104.2 |
| 30 | C10AO + Suc. | 9.9 | 22.3 | 38.3 | 67.0 | 52.6 |
| 31 | 0.125% CPC 1H₂O + 0.125% NaHCO₃ in water | 44.5 | 100.0 | | | |

*% Increase = [(Cf − Ci)/Ci] × 100
where Cf = amount CPC adsorbed in system with sweetener + C10AO
Ci = amount CPC adsorbed in system with sweetener and no C10AO As shown from the data presented in Table 7, the addition of the amine oxide to the various sweeteners in accordance with the present invention provided a dramatic increase in cetylpyridinium chloride absorption.

EXAMPLE 6

Toothpaste compositions identified by samples 32–39 shown in Table 8 were prepared containing one or more components selected from silica, amine oxide and sweetener as shown in Table 9. A control sample was prepared and identified as Sample 40.

TABLE 8

| Component | Amount (Wt. %) |
|---|---|
| Glycerin | 15 |
| Natrosol 250 M | 1 |
| 70% (wt./wt.) Sorbitol in water | 19 |
| Na-MFP | 1.153 |
| CPC monohydrate | 0.5 |
| Al₂O₃ | 7 |
| NaHCO₃ | 5 |
| Silica | 22.047 |
| Flavor | 1 |
| Decylamine oxide | 0.9 |
| Sweetener | 0.31 |
| Water | q.s. to 100% |

TABLE 9

| Sample | Description | CDC adsorbed (μg/disk) | % Activity (amount CPC/ max CPC adsorbed) |
|---|---|---|---|
| 32 | S700 alone | All values were below the detection limit of 2.5 μg/disk | <5.6 |
| 33 | C10AO + S700 | | |
| 34 | Grace A alone | | |
| 35 | C10AO + Grace A | | |
| 36 | C10AO + Sacc + S700 | | |
| 37 | C10AO + Suc + S700 | | |
| 38 | C10AO + Sacc + Grace A | | |
| 39 | C10AO + Suc + Grace A | | |
| 40 | 0.125% CPC monohydrate + 0.125% NaHCO₃ in water | 44.5 | 100.0 |

S700 = Sylodent 700 (A standard silica)
Grace A = Modified silica from Grace

As shown from the results in Table 9, the presence of silica had a significant adverse affect on cetylpyridinium chloride adsorption.

What is claimed:

1. A toothpaste composition comprising:

a) the absence of an anionic sweetener;

b) an antibacterial effective amount of cetylpyridinium chloride;

c) a mixture of toothpaste forming components other than cetylpyridinium chloride, including active components, passive components, or both, at least one of which is anionic, at least one amphoteric surfactant and at least one sweetener selected from the group consisting of cationic, non-ionic and amphoteric sweeteners, whereby in the absence of the amphoteric surfactant, the anionic toothpaste forming components would bind to the cetylpyridinium chloride preventing it from being attracted to negatively charged tooth surfaces, and because of the presence of the amphoteric surfactant the cetylpyridinium chloride is able to effectively bind to the negatively charged tooth surfaces.

2. The toothpaste composition of claim 1 wherein the amphoteric surfactant is selected from the group consisting of amino acids and amine oxides.

3. The toothpaste composition of claim 2 wherein the amphoteric surfactants are selected from those having the Formula (I)

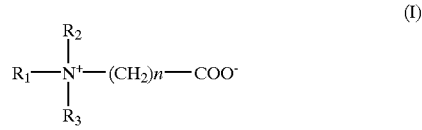

where $R_1$ and $R_2$ are independently an alkyl group having from 1 to 4 carbon atoms, $R_3$ is a group $R_a$ or $(R_a-C(O)NH)-(CH_2)_m$ in which m is an integer of from 1 to 4, and $R_a$ is an alkyl of from 8 to 20 carbons; and n is an integer of from 1 to 4.

4. The toothpaste composition of claim 3 wherein $R_a$ is a mixture of $C_{14}$–$C_{16}$ alkyl groups.

5. The toothpaste composition of claim 3 wherein m is 3.

6. The toothpaste composition of claim 3 wherein the surfactant is selected from the group consisting of cocobetaine and cocamidopropyl betaine and combinations thereof.

7. The toothpaste composition of claim 2 wherein the surfactants are those having the Formula (II)

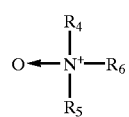
(II)

wherein $R_4$ and $R_5$ which may be the same or different are each independently selected from the group consisting of an alkyl group having 1 to 4 carbon atoms, and $R_6$ is an alkyl group having from 6 to 10 carbon atoms, which is unsubstituted or substituted by at least one $C_1$–$C_4$ alkyl group.

8. The toothpaste composition of claim 7 wherein the surfactant is selected from the group consisting of didecylmethylamine oxide, cocamidopropyl dimethylamine oxide, ether amine oxides and combinations thereof.

9. The toothpaste composition of claim 7 wherein the surfactant is selected from the group consisting of N,N-dimethyldodecylamine oxide, N,N-dimethyldecylamine oxide and combinations thereof.

10. The toothpaste composition of claim 1 wherein the sweetener is sucralose.

11. The toothpaste composition of claim 1 comprising at least one toothpaste forming component selected from the group consisting of whiteners, flavorants, humectants, desensitizing agents, thickening agents, abrasives and fluoride providing compounds.

12. The toothpaste composition of claim 11 wherein the abrasive material is selected from the group consisting of sodium metaphosphate, potassium metaphosphate, tricalcium phosphate, dicalcium phosphate dihydrate, anyhydrous dicalcium phosphate, calcium pyrophosphate, zinc orthophosphate, alumina, hydrated alumina, aluminum silicate, bentonite, calcium carbonate, and sodium bicarbonate.

* * * * *